United States Patent [19]

Mandai et al.

[11] Patent Number: 5,693,788

[45] Date of Patent: *Dec. 2, 1997

[54] DESICCATION AND PREVENTION OF RETROGRADATION USING TREHALOSE

[75] Inventors: Takahiko Mandai; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. No. 5,543,513.

[21] Appl. No.: 591,367

[22] Filed: Jan. 25, 1996

Related U.S. Application Data

[62] Division of Ser. No. 393,245, Feb. 23, 1995, Pat. No. 5,543,513, which is a continuation of Ser. No. 159,600, Dec. 1, 1993, abandoned.

[30] Foreign Application Priority Data

Dec. 2, 1992 [JP] Japan .................................. 4-356600

[51] Int. Cl.⁶ .............................. C07H 3/04; A23L 3/3562
[52] U.S. Cl. .................. 536/123.13; 536/102; 536/124; 514/53; 252/194; 426/443
[58] Field of Search ........................... 536/123.13, 124, 536/102; 514/53; 252/194; 426/443

[56] References Cited

U.S. PATENT DOCUMENTS

| | | | |
|---|---|---|---|
| 4,307,229 | 12/1981 | Liave et al. | 536/119 |
| 4,666,527 | 5/1987 | Ito et al. | 127/60 |
| 4,678,812 | 7/1987 | Bollin, Jr. et al. | 514/777 |
| 4,812,444 | 3/1989 | Mitsuhashi et al. | 514/53 |
| 4,870,059 | 9/1989 | Mitsuhashi et al. | 514/53 |
| 4,880,635 | 11/1989 | Janoff et al. | 424/450 |
| 4,885,172 | 12/1989 | Bally et al. | 424/417 |
| 4,891,319 | 1/1990 | Roser | 435/188 |
| 5,047,245 | 10/1991 | Bally et al. | 424/450 |
| 5,059,518 | 10/1991 | Kortright et al. | 435/6 |
| 5,082,664 | 1/1992 | Lenk et al. | 424/450 |
| 5,089,181 | 2/1992 | Hauser | 424/1.21 |
| 5,242,792 | 9/1993 | Rudolph et al. | 435/2 |
| 5,543,513 | 8/1996 | Mandai et al. | 536/123.13 |

FOREIGN PATENT DOCUMENTS

| | | |
|---|---|---|
| 0297887 | 1/1989 | European Pat. Off. . |
| 486315A2 | 11/1991 | European Pat. Off. . |
| 13624087 | 12/1985 | Japan . |
| 15253687 | 12/1985 | Japan . |
| 15253787 | 12/1985 | Japan . |
| 17949092 | 11/1990 | Japan . |
| 8601103 | 2/1986 | WIPO . |
| 8700196 | 1/1987 | WIPO . |

OTHER PUBLICATIONS

Jeffrey et al., *Carbohydr. Res.*, 1985, 137, 21–30.
Levine et al., *BioPharm*, May 1992, 5(4), 36–40.
Hakko–Kyokai–Shi, vol. 17, pp. 106–115 (1959).
G. Birch, Journal of the Chemical Society, pp. 3489–3490 (1965).

*Primary Examiner*—Kathleen K. Fonda
*Attorney, Agent, or Firm*—Browdy and Neimark

[57] ABSTRACT

Disclosed are a novel desiccant containing a non-reducing anhydrous trehalose as an effective ingredient; a dehydration of hydrous matters, e.g. food products, pharmaceuticals and cosmetics, therewith; and dehydrated products obtained by the dehydration. Such hydrous matters are dehydrated without causing alteration or deterioration by incorporating anhydrous trehalose into the hydrous matters to convert the anhydrous trehalose into hydrous crystalline trehalose. The anhydrous trehalose are anhydrous crystalline trehalose and hydrous amorphous trehalose.

12 Claims, 3 Drawing Sheets

DESICCATION AND PREVENTION OF RETROGRADATION USING TREHALOSE

This is a division of parent application Ser. No. 08/393, 245 filed Feb. 23, 1995, now U.S. Pat. No. 5,543,513, which is a continuation of Ser. No. 08/159,600, filed Dec. 1, 1993, now abandoned.

FIELD OF THE INVENTION

The present invention relates to a desiccant comprising anhydrous trehalose as an effective ingredient, as well as to a method for dehydrating hydrous matters with said desiccant and to dehydrated products obtainable by the method.

DEFINITION

Throughout the specification, the wording "w/w %" will be abbreviated as "%", unless specified otherwise.

BACKGROUND OF THE INVENTION

As disclosed by the present inventors in Japanese Patent Laid-Open Nos.136,240/87, 152,536/87 and 152,537/87, hconventional dehydration methods using anhydrous saccharides are those wherein a dehydrating activity is utilized, said activity being exerted by allowing an anhydrous saccharide to absorb moisture from a hydrous matter to convert the anhydrous saccharide into a hydrous crystalline form. Unlike heat drying, these methods require no heating conditions and have a merit of converting hydrous matters into dehydrated products without deterioration or degeneration of their quality.

It was found that among the above-mentioned methods the method using anhydrous aldohexoses such as anhydrous glucose or galactose as disclosed in Japanese Patent Laid-Open No.152,536/87, attains a satisfiable dehydration of a relatively-large amount of water and readily induces the maillard reaction because such an anhydrous aldohexose has a reducing property and a relatively-high reactivity to substances such as amino acids or peptides; and because of these, there exists an anxiety about the stability of the resultant dehydrated product. It was also found that anhydrous aldohexoses are not convertible into hydrous crystalline aldohexoses even at an elevated humid condition, and only exert a poor dehydrating-activity. It was found that in case of using anhydrous maltose as disclosed in Japanese Patent Laid-Open No.136,240/87 and in case of using anhydrous paratinose as disclosed in Japanese Patent Laid-Open No.152,537/87, there still remains an anxiety about a long-term stability of the resultant dehydrated product because anhydrous maltose and anhydrous paratinose, even if they have a relatively-low reducing activity, are basically reducing sugars. It was also found that the amount of moisture absorbed by anhydrous maltose or anhydrous paratinose is relatively low, i.e. about 5 w/w % with respect to the amount of the anhydrous maltose or the anhydrous paratinose, and because of this such saccharides have a demerit that it should be used as a desiccant in a relatively-large amount.

It may be speculated that anhydrous non-reducing glycosylfructosides such as anhydrous raffinose, anhydrous erlose and anhydrous melezitose as disclosed in Japanese Patent Laid-Open No.152,537/87 have no reducing activity and do not react with amino acids and peptides, and this imparts them a satisfactory shelf-life without inducing the maillard reaction. Anhydrous glycosylfructosides, however, have a fructoside bond with a relatively-low acid tolerance in their molecules, and this may lead to an estimation that the anhydrous glycosylfructosides are not necessarily suitable as a desiccant for acid hydrous matters. In this case, there still remains an anxiety about stability in the resultant dehydrated products.

SUMMARY OF THE INVENTION

In order to overcome these demerits of conventional dehydration methods using saccharides, the present inventors have screened natural non-reducing anhydrous saccharides and studied to establish a desiccant with a satisfiable dehydrating activity, as well as its uses.

As a result, the present inventors found that among the non-reducing anhydrous saccharides as tested anhydrous trehalose (throughout the specification, "α,α-trehalose" and "α,β-trehalose" are designated as "trehalose" and "neotrehalose" respectively) dehydrates a relatively-large amount of water and exerts a strong dehydrating activity, and that the resultant dehydrated products prepared with the anhydrous trehalose are extremely stable. These render the anhydrous trehalose useful as a desiccant in a variety of fields. In other words, the present inventors found that when anhydrous trehalose is incorporated into hydrous matters such as hydrous food-products and hydrous pharmaceuticals, the anhydrous trehalose is converted into hydrous crystalline trehalose which absorbs a relatively-large amount of water in the hydrous matters and to exerts as a desiccant a strong dehydrating-activity. The anhydrous trehalose is used in a variety of hydrous matters including hydrous acidic matters. The present inventors also confirmed that anhydrous trehalose is used in the preparations of dehydrated products such as dehydrated food products with a satisfactory taste and quality, as well as dehydrated pharmaceuticals with a relatively-high activity and stability. Thus, the present inventors accomplished this invention.

BRIEF DESCRIPTION OF THE ACCOMPANYING DRAWINGS

DESCRIPTION OF THE PREFERRED EMBODIMENTS

Figure 1:
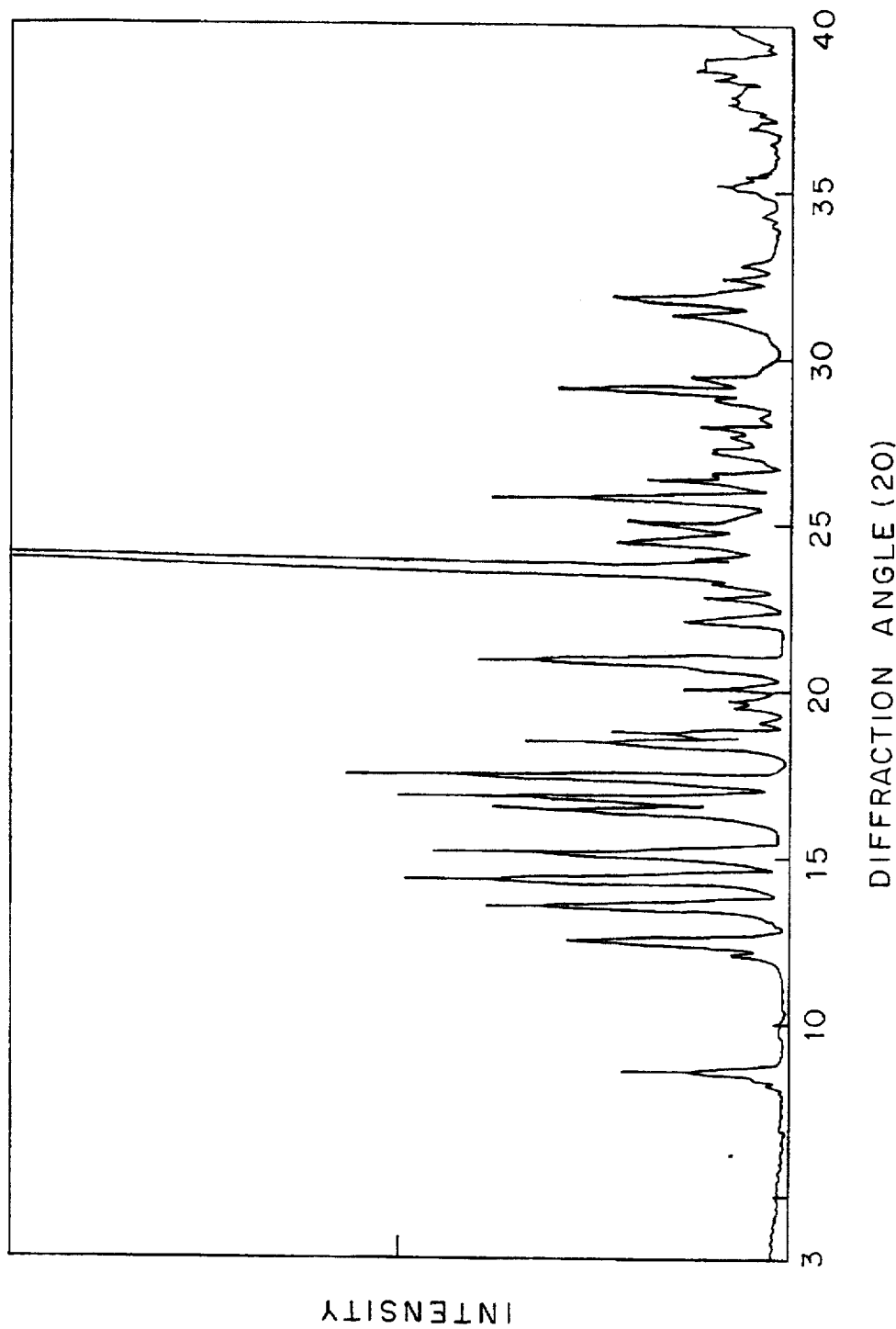
FIG. 1 shows a powder x-ray diffraction figure of hydrous crystalline trehalose.

The present inventors screened desiccants using non-reducing saccharides and chose as the desiccant anhydrous trehalose which had not been deemed useful for that purpose. The present inventors first accomplished the dehydration method for a hydrous matter by incorporating anhydrous trehalose thereinto.

The dehydration method according to the present invention can be arbitrarily used to dehydrate hydrous matters, especially, those which contain free water different from a bonded water such as water incorporated in a crystalline structure. For example, the present method can be advantageously used to decrease the moisture content in atmosphere of a moistureproof package enclosing a dehydrated food product, as well as to decrease the moisture content in a variety of hydrous matters such as food products, pharmaceuticals, cosmetics, chemicals for industrial uses, and their materials or intermediates.

The present inventors found that when anhydrous trehalose is incorporated into the above-mentioned hydrous matters, it entraps about 10 w/w % moisture from the hydrous matters in hydrous crystalline trehalose, which is 2-fold higher than that attained with anhydrous maltose, and substantially eliminates the moisture from the hydrous matters or even brings them to dryness.

It was also found that the relative humidity in a moistureproof package enclosing a dehydrated food product, for example, "ajitsuke-nori" (seasoned laver) and cookie, is extremely decreased by placing in the moistureproof package a small moisture-permeable paper-bag injected with anhydrous trehalose, whereby the quality of the dehydrated food product or powdery product is stabilized over a relatively-long period of time.

Since anhydrous trehalose neither becomes sticky nor oozes during or after conversion into hydrous crystalline trehalose, dehydrated food products and moistureproof packages are free from staining. Anhydrous trehalose prevents the solidification of powdery products and their adhesion to moistureproof packages. In addition, trehalose per se causes no side effect because it is a non-toxic and harmless natural-sweetener.

According to the present invention, high-quality food products with a substantially-decreased moisture in the form of, for example, massecuite or powder, can be readily prepared by incorporating anhydrous trehalose into food products with a relatively-high moisture content in liquid or paste form, for example, brandy, vinegar, royal jelly, fresh cream and mayonnaise to convert the anhydrous trehalose into hydrous crystalline trehalose.

The dehydration method according to the present invention is characterized in that it utilizes a stable non-reducing saccharide, i.e. anhydrous trehalose, and requires no heat treatment such as heat drying, whereby a relatively-high moisture content food product in liquid or paste form is readily converted into a dehydrated product with a decreased moisture and a satisfiable flavor and taste without alternating or deteriorating the food product.

It was found that dehydrated food products in which anhydrous trehalose has been partially converted into hydrous crystalline trehalose, i.e. dehydrated food products containing anhydrous trehalose are obtainable by adding an excessive amount of anhydrous trehalose to material food products in an amount of which exceeds the moisture content in the food products; and that when the dehydrated food products are injected into moistureproof packages the moisture in the packages is entrappad by the anhydrous trehalose for its conversion into hydrous crystalline trehalose, whereby the relative humidity in the packages is decreased by a large margin and the atmosphere in the packages is kept at a relatively-high dryness. As a result, it was found that the dehydrated food products obtained by the present invention are prevented from bacterial contamination, as well as alteration or deterioration such as hydrolysis, souring and browning, and because of this the products with a satisfactory quality and taste are stably retained for a relatively-long period of time.

In the preparation of dehydrated pharmaceuticals with a high quality and a substantially-decreased moisture level, for example, those in the form of massecuite and powder are readily prepared by incorporating anhydrous trehalose into pharmaceuticals in liquid form such as those containing lymphokines and antibiotics, as well as those in paste form such as ginseng extract and snapping turtle extract, to convert the anhydrous trehalose into hydrous crystalline trehalose.

The preparations can provide a high quality and stable dehydrated-pharmaceuticals because they do not require severe conditions such as heat drying, and because the anhydrous trehalose acts as a desiccant and stabilizer.

Conventional stabilizers such as water-soluble high molecular-weight substances substantially do not waste energy for their drying so that they can be favorably added to the dehydrated pharmaceuticals to improve their qualities and stabilities.

The present invention can be advantageously practiced in the preparations of solid pharmaceuticals by placing a prescribed amount of anhydrous trehalose, for example, in a vial; adding to the vial an aqueous solution containing a biologically active substance such as a lymphokine or a hormone in an amount of which is slightly-lower than the moisture content required for the complete conversion of the anhydrous trehalose into hydrous crystalline trehalose; and cap sealing the vial.

In this case, it was found that the anhydrous trehalose dehydrates the aqueous solution containing a biologically active substance, and dehumidifies the atmosphere in the vial.

It was also found that as a consequence the present invention facilitates the preparation of dehydrated solid pharmaceuticals, and still that the solid pharmaceuticals retain their high-quality over a relatively-long period of time and readily dissolve in water on use.

High quality and stable solid pharmaceuticals can be advantageously prepared by mixing a prescribed amount of anhydrous trehalose while stirring with a prescribed amount of an aqueous solution containing a biologically active substance, placing the resultant powdery product in a container, and sealing the container. If necessary, the powdery product can be suitably formed into a granule or a tablet in usual manner.

As described above, unlike conventional desiccants such as a silica gel and a calcium oxide, the present desiccant using anhydrous trehalose is edible, and, therefore it is assimilable and alimentary in the body. It also acts as a stabilizer for biologically active substances.

The present inventors studied on the preparation of anhydrous trehalose, especially, the preparation of a powdery anhydrous trehalose.

The anhydrous trehaloses suitably used in the invention are, for example, anhydrous crystalline trehalose and anhydrous amorphous trehalose.

In *Journal of the Chemical Society*, pp.3,489–3,490 (1965), G. Birch reported a preparation of anhydrous crystalline trehalose by crystallizing it in pyridine. The preparation is, however, expensive because it requires an excessive amount of pyridine as a solvent, and not satisfiable in view of the food sanitation.

In view of the prior art, the present inventors studied the preparation of a powdery anhydrous crystalline trehalose and established the preparation thereof, e.g. a preparation which comprises providing an aqueous solution in which a commercially available hydrous trehalose has been dissolved or providing an aqueous trehalose solution prepared by extracting trehalose from yeasts and purifying the resultant extract in accordance with a method as described by M. Hayashibe and K. Aso in Hakko-Kyokai-shi, Vol.17, pp.106–115 (1959); preparing such an aqueous solution into a syrup with a relatively-high concentration and a moisture content lower than about 109, preferably, 2.0 or higher but lower than 9–5%; keeping the syrup in the presence of a seed crystal at a temperature of 50°–160° C. to crystallize anhydrous crystalline trehalose; and pulverizing the resultant crystal.

The pulverizing methods usable in the invention are suitably chosen from conventional methods such as a block pulverization, extruding granulation, fluidized-bed granulation and spray-drying. The anhydrous amorphous trehaloses usable in the invention can be prepared from a commercially-available hydrous crystalline trehalose or a concentrated solution of a high-purity trehalose extracted and purified from yeasts.

In the case of using hydrous crystalline trehalose as a material for anhydrous trehalose, the hydrous crystalline trehalose is dissolved in water, dried in vacuo or at an atmospheric pressure and at a temperature of about 100°–160° C., and pulverized to obtain anhydrous trehalose. In the case of using an aqueous solution of a high-purity trehalose as a material for anhydrous trehalose, for example, an about 70–90% trehalose syrup can be advantageously dried in vacuo or at an atmospheric pressure, and pulverized into anhydrous trehalose. Alternatively, an about 60–85% trehalose syrup can be advantageously subjected to a spray-drying such as a high-pressure nozzle method and a rotating disk method to directly obtain a powdery anhydrous trehalose.

The powdery anhydrous trehaloses usable in the invention are non-reducing saccharide powders in white having (i) a satisfactorily high-quality and low-sweetness; (ii) a relatively-low moisture content or substantially anhydrous, usually, 3% or lower, preferably, 2% or lower on the Karl Fischer's method; and (iii) a substantial free-flowing ability which may be varied dependently on their particle size and shape.

The anhydrous trehalose as referred to in the invention includes any substantially anhydrous trehalose as long as it absorbs moisture and converts into hydrous crystalline trehalose to exert a strong dehydrating activity. In order to augment the effect of anhydrous trehalose as a desiccant, trehalose can be formulated to coexist in a powdery anhydrous amorphous trehalose the lowest possible amount of hydrous crystalline trehalose as a seed crystal, usually, in an amount lower than 5%, preferably, lower than one %, whereby the conversion rate of anhydrous trehalose into hydrous crystalline trehalose is improved.

It was found that the powdery anhydrous trehalose thus obtained acts as a desiccant with a strong dehydrating activity against hydrous matters in a manner such that it entraps and fixes the moisture contained in hydrous matters such as food products, pharmaceuticals, cosmetics and industrial chemicals when incorporated into the hydrous matters.

The present desiccant can be advantageously used to dehumidify and dry the atmosphere in a moistureproof package, as well as to prepare a high-quality dehydrated product in massecuite or powder form from a hydrous matter which is susceptible to alteration and deterioration during heat drying- or vacuum drying-step, as well as from those which are substantially difficult to dry.

The present desiccant can be suitably used to dehumidify and dry hydrous matters. For example, it can be used to prevent "ajitsuke-nori" and cookies from absorbing moisture, or advantageously incorporated into powdery products which readily absorb moisture to form solid products, for example, ready-mixed powders such as those of purine and hot cake; powdery seasonings such as salt, sugar, powdered soy sauce, powdered "miso" (soybean paste), powdered "sushi-su" (a vinegar), powdered "dashi-no-moto", powdery mixed seasoning, powdered paprika, powdered garlic, powdered cinnamon, powdered nutmeg, powdered pepper and powdered sage; and other powdery products such as powdered yeast extract, powered milk, powdered yogurt, powdered cheese, powdered juice, powdered herb, powdered vitamin, granulated soup, granulated bouillon, fish flour, blood meal, bone meal, powdered agent of lactic acid bacteria, powdered enzyme and granulated digestive; followed by placing the resultant dehydrated product into a package, whereby (i) the relative humidity within the package is decreased, and (ii) the resultant product is prevented from solidification and adhesion to the package, and satisfactorily retains its quality for a relatively-long period of time.

The desiccant according to the present invention can be suitably used to dehydrate hydrous matters such as organs, tissues, cells, homogenates, extracts and components derived from animals, plants and microorganisms, as well as preparations therefrom.

When a hydrous matter is a food product, or its materials or intermediates exist in liquid or paste form, a stable and tasty dehydrated food product can be readily prepared according to the invention. Examples of such a hydrous matter are agricultural products such as fresh fruit, juice, vegetable extract, soybean milk, sesame paste, nut paste, "nama-an" (unsweetened bean jam), gelatinized starch paste and wheat flour; marine products such as sea urchin paste, oyster extract and sardine paste; poultry and livestock products such as fresh egg, lecithin, milk, whey, fresh cream, yogurt, butter and cheese; hydrous seasonings such as maple syrup, honey, "miso" (soybean paste), soy sauce, mayonnaise, dressing, bonito extract, meat extract, tangle extract, chicken extract, beef extract, yeast extract, mushroom extract, licorice extract, stevia extract, enzymatically processed product thereof and seasoning liquid for pickles; liquors such as Japanese sake, wine, brandy, whisky and medical liqueur; soft drinks such as a tea, green tea and coffee; hydrous spices such as those extracted from peppermint, "wasabi" (Japanese horseradish), garlic, mustard, "sansho" (Japanese pepper tree), cinnamon, sage, laurel, pepper and citrus fruit; hydrous coloring agents such as those extracted from madder, annatto (*Bixa orellana*), turmeric, paprika, red beet, safflower, cape jasmine, saffron and extract from microorganism of the genus *Monascus*; hydrous emulsifiers such as a fatty acid sugar ester, glycerine, fatty acid ester and sorbitan fatty acid ester; and preservatives in liquid or paste form such as a smoke solution and a fermented solution.

The dehydrated products obtained in this way, for example, a powdered agricultural- or poultry-product, powdered oil and fat, powdery flavor and powdery coloring agent can be conveniently used, for example, as a natural bulk flavor excellent in taste and flavor, in various food products, for example, seasonings such as a mayonnaise and soup stock; confectioneries such as a hard candy and cake; and materials for food products such as a hot cake mix and instant juice.

When a hydrous matter is a pharmaceutical, or its material or intermediate, it can be readily prepared into a stable and highly-active pharmaceutical according to the present invention without inactivating the effective ingredients. Examples of such a hydrous matter are a solution containing lymphokine such as an α-, β- or γ-interferon, tumor necrosis factor-α (TNF-α), tumor necrosis factor-β (TNF-β), macrophage migration inhibitory factor, colony-stimulating factor, transfer factor and interleukin 2; a solution containing hormone such as insulin, growth hormone, prolactin, erythropoietin and follicle-stimulating hormone; a solution containing a biological preparation such as BCG vaccine, Japanese encephalitis vaccine, measles vaccine, live polio vaccine, smallpox vaccine, tetanus toxoid, Trimeresurus antitoxin and human immunoglobulin; a solution containing an antibiotic such as penicillin, erythromycin, chloramphenicol, tetracycline, streptomycin and kanamycin sulfate; a solution containing a vitamin such as thiamine, riboflavin, L-ascorbic acid, liver oil, carotenoid, ergosterol and tocopherol; a solution containing an enzyme such as lipase, elastase, urokinase, protease, γ-amylase, isoamylase, glucanase and lactase; an extract such as ginseng extract, snapping turtle extract, chlorella extract, aloe extract and propolis extract; a paste of cell or minute infectious agent such as those of virus, lactic acid bacterium and yeast; and a liquid or paste such as royal jelly.

In order to dehydrate hydrous matters such as a cosmetic and its materials or intermediates, a high-quality cosmetic can be readily prepared by dehydrating a hydrous matter such as a fresh egg, lecithin, fresh cream, honey, licorice extract, flavor, coloring agent or an enzyme similarly as in the cases of food products and pharmaceuticals.

The cosmetic thus obtained can be advantageously used as a skin- or hair-treatment, as well as a hair restorer. When a dehydrated product is of an enzyme, it can be advantageously used as a therapeutic agent, digestive and enzymatic detergent, as well as a catalyst for the preparations of food products, pharmaceuticals and industrial materials.

Any conventional method such as mixing, kneading, dissolving, permeating, soaking, sprinkling, coating, spraying, crystallizing and injecting can be suitably employed as a method to incorporate anhydrous trehalose into hydrous matters before the completion of the processings of the objective dehydrated products.

Although the amount of anhydrous trehalose to be incorporated into a hydrous matter is varied depending on the moisture content and property of the hydrous matter, it is generally 0.01–200 parts by weight, desirably, 0.01–50 parts by weight to one part by weight of the hydrous matter. If necessary, the anhydrous trehalose may be incorporated into a hydrous matter after the hydrous matter has been partially dehydrated or concentrated by conventional method. In such a case, in order to improve the quality of the objective dehydrated-products such as food products, pharmaceuticals and cosmetics, an adequate flavor-imparting agent, coloring agent, taste-imparting agent, stabilizer and/or filler can be suitably used in combination with the anhydrous trehalose.

Examples of such a stabilizer are water-soluble polymers which have been hardly deemed to be dehydrated, and not limited to a relatively-low molecular-weight compound such as an antioxidant because the present method for dehydration employs anhydrous trehalose with a strong dehydrating activity. Examples of such a water-soluble polymer suitably used as a stabilizer in the invention are soluble starch, dextrin, pullulan, elsinan, dextran, xanthan gum, gum arabic, locust bean gum, guar gum, tragacanth gum, carboxymethyl starch, hydroxyethyl cellulose, pectin, agar, gelatin, albumin and casein.

When such a water-soluble polymer is used as a stabilizer, a dehydrated food product containing microcrystals of hydrous crystalline trehalose can be prepared by first dissolving a water-soluble polymer to homogeneity in a hydrous matter in liquid or paste form, then incorporating anhydrous trehalose to homogeneity into the resultant solution by a method such as mixing or kneading.

The product thus obtained retains the flavor and effective components of the material hydrous matter because the flavor and effective components are coated with a membrane of the above-mentioned water-soluble polymer, or enclosed in a microcapsule surrounded by the membrane together with the microcrystals of hydrous crystalline trehalose. Because of this, the flavor and effective components are prevented from volatilization and deterioration, and stably retained in the microcapsule. If necessary, cyclodextrins, which form an inclusion complex with the flavor and the effective components, can be suitably used as a water-soluble polymer in combination with the anhydrous trehalose.

The cyclodextrins usable in the invention are not restricted to those with the highest possible purity, and may be those with a relatively-low purity which can be hardly dried and pulverized. For example, syrups of a partial starch hydrolyzate containing cyclodextrins together with a large amount of maltodextrins can be favorably used. The methods to prepare dehydrated products usable in the present invention, especially, those to prepare powdery products are varied. For example, dehydrated products or powdery products can be prepared by a method comprising homogeneously mixing a hydrous matter having a relatively-high moisture content such as food products, pharmaceuticals, cosmetics and their materials or intermediates with anhydrous trehalose to obtain a mixture having a moisture content of about 40% or lower, preferably, 10–30%; placing the mixture in a container; allowing the container to stand at about 10°–50° C., e.g. at an ambient temperature, for about 0.1–5 days to solidify the mixture while the anhydrous trehalose is permitted to convert to hydrous crystalline trehalose; and cutting or pulverizing the resultant solid product. If necessary, a drying step and/or a classification step may be added to the cutting or pulverizing step. Furthermore, powdery products can be directly obtained by subjecting a mixture of a hydrous matter and anhydrous trehalose onto a spray-drying, etc.

Such a powdery product can be also prepared by a method (I) comprising spraying a prescribed amount of a hydrous matter in liquid or paste form to anhydrous trehalose in a state of flux, granulating the resultant mixture while the hydrous matter is in contact with the anhydrous trehalose, and, if necessary further ageing the resultant granule at a temperature of about 30°–60° C. for about 0.1–10 hours to convert the anhydrous trehalose into hydrous crystalline trehalose; and a method (II) comprising mixing or kneading anhydrous trehalose with a hydrous matter in liquid or paste form, and spraying the resultant mixture instantly or after the initiation of the conversion of the anhydrous trehalose into hydrous crystalline trehalose. If necessary, the powdery product thus obtained may be further aged similarly as in method (I) to convert the anhydrous trehalose into hydrous crystalline trehalose. Methods (I) and (II) can be suitably employed in the invention as a mass production of a powdery dehydrated-product.

In the case of such a spray-drying, it can be advantageously practiced to coexist with anhydrous trehalose the lowest possible level of hydrous crystalline trehalose as a seed crystal in order to promote the conversion of the anhydrous trehalose into hydrous crystalline trehalose, whereby the ageing period of time is satisfactorily shortened or the ageing step can be even eliminated. The powdery dehydrated-product thus obtained can be used alone, and, if necessary it can be formed into a product in liquid or paste form in combination with a filler, excipient, binder and/or stabilizer, and freely formed into a granule, tablet, capsule, rod, plate or cube.

Sugar-coating products can be advantageously prepared by coating a core or a center, for example, a food product such as a peanut, almond or candy, or a pharmaceutical intermediate in the form of a granule or a crude tablet, with an aqueous solution containing about 60–90% of anhydrous trehalose, preferably, a solution containing anhydrous trehalose together with an adequate amount of a binder such as a water-soluble polymer to crystallize hydrous crystalline trehalose on the core.

Generally, starch requires a relatively-large amount of moisture in order to swell and gelatinize. For this reason, gelatinized starch is highly susceptible to bacterial contamination. Anhydrous trehalose can be favorably used as a desiccant for dehydrating such a gelatinized starch. For example, "gyuhi" (a gelatinized starch in paste form) is prevented from bacterial contamination by incorporating anhydrous trehalose into the gelatinized starch to convert the anhydrous trehalose into hydrous crystalline trehalose, whereby the moisture in the gelatinized starch is substantially decreased.

Anhydrous trehalose readily disperses homogeneously into gelatinized starch and acts as a retrogradation-preventing agent, and because of this anhydrous trehalose satisfactorily prolongs the shelf life of a variety of processed food products containing gelatinized starch.

Anhydrous trehalose can be used as a food preservative, stabilizer and quality-improving agent in hydrous food products having a relatively-high moisture content such as a peeled banana, orange, sliced steamed-potato, opened horse-mackerel, *Pacific saury*, raw noodle, boiled noodle and bean-jam cake by sprinkling anhydrous crystalline trehalose as an anhydrous trehalose over the surface of the hydrous food products to convert the anhydrous crystalline trehalose into hydrous crystalline trehalose, whereby the moisture on the surface of the hydrous food products is substantially decreased, and their qualities and shelf lives are satisfactorily improved and prolonged. In this case, when a more prolonged shelf life is required, the anhydrous crystalline trehalose can be suitably used in combination with lactic acid, citric acid and/or ethanol; and, if necessary the resultant dehydrated products may be subjected to a vacuum package, a gas flush package or a cold storage.

Anhydrous trehalose has a relatively-high affinity for alcohols. This property renders anhydrous trehalose useful as a desiccant to remove moisture contained in alcohols such as methanol, ethanol, butanol, propylene glycol, glycerin and polyethylene glycol, as well as in alcohol-soluble substances.

For example, dehydrated liquors in massecuite or powdery form, which retain the effective ingredients and flavors of liquors, can be prepared by dehydrating with anhydrous trehalose liquors such as "sake" (Japanese rice wine), "sho-chu" (low-class distilled spirits), wine, brandy, whisky and vodka. The powdery dehydrated-liquors thus obtained can be used in confectioneries and ready-mix powders, or used by dissolving them in water prior to their use.

In this case, anhydrous trehalose can exert a satisfactory effect as a desiccant and stabilizer, as well as a mild sweetener, filler and adequate viscosity-imparting agent.

Effective elements such as iodine can be stably retained by mixing an alcohol-soluble substance such as iodine with anhydrous trehalose, and mixing the resultant mixture with an aqueous solution containing a water-soluble high molecular-weight substance to convert the anhydrous trehalose into hydrous crystalline trehalose. Thus, an ointment in massecuite form having an adequate viscosity, extensibility and adhesiveness can be favorably prepared.

Dehydrated products, for example, powdery food products such as those of oils and fats, seasonings, flavors and color-imparting agents; powdery cosmetics; and powdery pharmaceuticals such as those of vitamins and hormones can be favorably prepared by incorporating anhydrous trehalose into their material products to convert it into hydrous crystalline trehalose while impregnating or mixing the anhydrous trehalose with a latex, an emulsified product or a hydrous oil-soluble substance.

In this case, anhydrous trehalose acts as a desiccant, and the converted hydrous crystalline trehalose acts as a stabilizer, preservative, filler and carrier.

Anhydrous trehalose can be suitably used in food products containing oil-soluble substances such as a chocolate and cream filling which are apt to be readily damaged by moisture. In this case, anhydrous trehalose is used as a desiccant, as well as an agent for improving the processibility, flavor and meltability in the mouth. The dehydrated food products thus obtained has a relatively-long shelf-life.

As described above, the present invention was made based on the findings that anhydrous trehalose strongly dehydrates hydrous matters, and that the resultant dehydrated products have a satisfiable stability. By using the anhydrous trehalose as a desiccant, high-quality food products and cosmetics with a decreased moisture-content can be favorably prepared without deteriorating or losing their flavors and tastes; and high-quality pharmaceuticals and cosmetics with a decreased moisture-content can be favorably prepared without decomposing or losing their effective ingredients or activities.

In addition to the aforementioned specific properties, anhydrous trehalose as a natural sweetener is readily assimilated and utilized by the body without fear of causing cariogenicity and increasing the blood cholesterol-level, and has substantially the same level of nutritive value as maltooligosaccharides. Anhydrous trehalose has a mild sweetness, body-imparting ability, gloss-imparting ability, viscosity-imparting ability and moisture-retaining ability, and these render it advantageously useful in food products, pharmaceuticals and cosmetics.

The followings are illustrative of additional uses of anhydrous trehalose:

Anhydrous trehalose can be used as a seasoning with a strong dehydrating activity. If necessary, it can be used together with one or more other sweeteners, for example, powdered syrup, glucose, isomerized sugar, sucrose, maltose, honey, maple sugar, sorbitol, maltitol, dihydrocharcone, stevioside, α-glycosyl stevioside, sweet substance derived from *Momordica grosvenori* Swingle, glycyrrhizin, thaumatin, L-aspartyl L-phenylalanine methyl ester, saccharin, glycine and alanine; and/or a filler such as dextrin, starch and lactose.

Anhydrous trehalose, a non-reducing saccharide, has features: (i) it has the inherent mild sweetness of trehalose; (ii) it well harmonizes with other materials having sour-, acid-, salty-, bitter-, astringent- and delicious-tastes, and (iii) it is highly acid- and heat-resistant. Thus, anhydrous trehalose can be favorably used in food products in general as a desiccant, as well as a sweetener, taste-improving agent and quality-improving agent.

Anhydrous trehalose is used as a desiccant, sweetener, taste-improving agent and quality-improving agent in seasonings such as soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbaizu" (a sauce of sugar, soy sauce and vinegar), "funmatsu-sushi-su"

(powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "Uakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar and coffee sugar.

Also, anhydrous trehalose can be freely used for dehydrating "wagashi" (Japanese cakes) such as "senbei" (a rice cracker), "arare-mochi" (a rice-cake cube), "okoshi" (a millet-and-rice cake), "gyuhi" (a rice paste), "mochi" (a rice paste), "manju" (a bun with a bean-jam), "uiro" (a sweet rice jelly), "an" (a bean jam), "Uokan" (a sweet jelly of beans), "mizu-Uokan" (a soft adzuki-bean jelly), "kingyoku" (a kind of yokan), jelly, pao de Castella and "amedama" (a Japanese toffee); confectioneries such as bakery products such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste and fruit paste; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; fish meat products such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips), "fugu-no-mirin-boshi" (a dried mirin-seasoned swellfish), and mashed and seasoned food of cod, sea bream and shrimp; "tsukudani" (foods boiled down in soy sauce) such as those of laver, edible wild plants, dried squid, fish and shellfish; daily dishes such as "nimame" (cooked beans), potato salad and "koribu-maki" (a tangle roll); milk products; canned and bottled products such as those of meat, fish meat, fruit and vegetable; alcoholic beverages such as synthetic sake, "zozyo-shu", fruit wine and liquors; soft drinks such as coffee, cocoa, juice, carbonated beverage, sour milk beverage and beverage containing a lactic acid bacterium; instant food products such as instant pudding mix, instant hot cake mix, juice power, instant coffee, "sokuseki-shiruco" (an instant mix of adzuki-bean soup with rice cake) and instant soup mix; as well as for sweetening the aforementioned food products and improving their tastes and qualities.

The following experiments explain the present invention in detail:

Experiment 1

Comparison of Dehydrating Activities of Non-reducing Saccharides and Stabilities of Dehydrated Products Prepared Therewith Non-reducing saccharides used in this experiment were sucrose, anhydrous crystalline trehalose, anhydrous amorphous trehalose, hydrous crystalline trehalose, anhydrous amorphous neotrehalose, hydrous crystalline neotrehalose, hydrous amorphous erlose, hydrous crystalline erlose, anhydrous amorphous raffinose, hydrous crystalline raffinose, anhydrous amorphous melezitose and hydrous crystalline melezitose. The sucrose, hydrous crystalline trehalose, hydrous crystalline erlose, hydrous crystalline raffinose and hydrous crystalline melezitose were the grades of commercially available reagents. The anhydrous crystalline trehalose and anhydrous amorphous trehalose were respectively prepared by the methods in Examples for reference 1 and 3. The anhydrous crystalline neotrehalose was prepared by the method in Experiment 2 as disclosed in Japanese Patent Laid-Open No. 179,490/92. The anhydrous amorphous neotrehalose, anhydrous amorphous erlose, anhydrous amorphous raffinose and anhydrous amorphous melezitose were respectively prepared by dissolving each of them in water, and drying the resultant solution in vacuo at an ambient temperature.

The non-reducing saccharides were studied on their dehydrating activities. A mixture, obtained by mixing 2 parts by weight of a plain yogurt with 8 parts by weight of one of the non-reducing saccharides, was placed in a container and allowed to stand at 25° C. overnight, followed by observing the macroscopic change of the resultant mixture. The dehydrating activities of the non-reducing saccharides were graded into 3 ranks, i.e. "High" meaning that it formed a complete solidification; "Low", that it formed an incomplete solidification; and "Non", that it showed no substantial change.

The completely solidified-products were studied on their stabilities: Each product was pulverized by a cutter to obtain a powdery product which was then granulated to give a granular size of about 100–150 μm. Thirty g aliquots of the granules were placed in plastic petri-dishes, and allowed to stand at 37° C. and a relative humidity of 70% for 2 weeks, followed by comparing the degree of color of the resultant product. The degree of color was defined as a difference between the absorbances at the wave lengths of 420 nm and 720 nm determined in a 10-cm cell with a supernatant prepared from a 30 w/v suspension of each solidified product. The stabilities of the dehydrated products were graded into the following ranks: "Superior" meaning that it showed a degree lower than 0.1; "Middle", that it showed a degree of 0.1 or higher but lower than 0.2; and "Inferior", that it showed a degree of 0.2 or higher.

The results were as shown in Table 1.

TABLE 1

| Sacchride | Macroscopic Change | Dehydrating activity | Stability of dehydrated product | Judgement |
| --- | --- | --- | --- | --- |
| Sucrose | Unchanged | Non | — | Control |
| Anhydrous crystalline trehalose | Completely solidified | High | Superior | Present invention |

TABLE 1-continued

| Sacchride | Macroscopic Change | Dehydrating activity | Stability of dehydrated product | Judgement |
|---|---|---|---|---|
| Anhydrous amorphous trehalose | Completely solidified | High | Superior | Present invention |
| Hydrous crystalline trehalose | Unchanged | Non | — | Control |
| Anhydrous amorphous neotrehalose | Incompletely solidified | Low | — | Control |
| Hydrous crystalline neotrehalose | Unchanged | Non | — | Control |
| Anhydrous amorphous erlose | Completely solidified | High | Inferior | Control |
| Hydrous crystalline erlose | Unchanged | Non | — | Control |
| Anhydrous amorphous raffinose | Completely solidified | High | Inferior | Control |
| Hydrous crystalline raffinose | Unchanged | Non | — | Control |
| Anhydrous amorphous melezitose | Incompletely solidified | Low | — | Control |
| Hydrous crystalline melezitose | Unchanged | Non | — | Control |

Note: In the Table, the symbol "—" means that the stability test of a mixture could not be done because of its incomplete solidification.

As evident from the results in Table 1, it was revealed that the anhydrous crystalline trehalose and the anhydrous amorphous trehalose had a strong dehydrating activity, and the dehydrated products prepared therewith had a Satisfactorily-high stability. Thus, anhydrous trehalose can be advantageously used as a desiccant.

Experiment 2

Dehydration by Anhydrous Trehalose

The dehydrating activities of anhydrous crystalline trehalose and anhydrous, amorphous trehalose as an anhydrous trehalose were studied i.e. the levels of their dehydrating activities and their dehydrating moisture-levels were studied in detail. As a control, hydrous crystalline trehalose was used. The procedure of this experiment was as follows: Each anhydrous trehalose obtained by the method in Experiment 1 was prepared into a powdery product having a grain size of about 100–150 μm. One g of the powdery product was placed in a plastic petri-dish having a diameter of 5 cm, and allowed to stand at 25° C. and a relative humidity of 70%, followed by measuring the moisture content (%) of the resultant product at a prescribed time-interval. The results were as shown in Table 2.

TABLE 2

| Trehalose | Time | | | | |
|---|---|---|---|---|---|
| | 0 | 4 | 8 | 24 | 72 |
| Anhydrous crystalline trehalose | 0.32 | 6.42 | 8.35 | 9.65 | 9.80 |
| Anhydrous amorphous trehalose | 0.83 | 8.20 | 9.57 | 9.80 | 9.80 |
| Hydrous crystalline trehalose | 9.57 | 9.60 | 9.62 | 9.64 | 9.70 |

As evident from the results in Table 2, it was revealed that the anhydrous trehaloses exerted a strong dehydrating activity, i.e. they entrapped moisture in the atmosphere in an amount of about 10% by weight of the anhydrous trehaloses, on a dry solid basis (d.s.b.). The anhydrous trehaloses were studied on their x-ray powder diffraction figures at a prescribed time-interval to reveal that they entrapped moisture and converted into hydrous crystalline trehaloses, and that the resultant products equilibrated and stabilized when absorbed about 10% moisture. An x-ray diffraction figure of hydrous crystalline trehalose was as shown in FIG. 1.

Similarly as above, the anhydrous trehaloses were allowed to stand at 25° C. and a relative humidity of about 90%, followed by measuring the moisture contents (%) of the resultant products at a prescribed time-interval. Similarly as in the above, the anhydrous trehaloses were converted into hydrous crystalline trehalose and equilibrated when absorbed about 10% moisture. In this case, the resultant products retained their powdery forms and no phenomenon such as sticking and flowing was observed.

Based on these properties, it was revealed that anhydrous trehalose can be advantageously used as a desiccant for food products, pharmaceuticals, cosmetics and their materials or intermediates.

Experiment 3

Comparison of Dynamics of Anhydrous Trehalose and Hydrous Crystalline Trehalose Against Gelatinized Starch Four parts by weight of powdery glutinous rice was suspended in 6 parts by weight of water, and the suspension was poured onto a wet close covered over the inside surface of a wooden container, and steamed up at 105° C. for 10 minutes to obtain a gelatinized starch. To the gelatinized starch was added 7 parts by weight of hydrous crystalline trehalose or anhydrous crystalline trehalose prepared by the method in Example for reference 1, and the resultant was mixed by a mixer until it showed homogeneity. Thereafter, the resultant mixture was sufficiently kneaded with 2 parts by weight of a starch hydrolyzate, formed, and mildly dried with a 40° C. hot-air for 2 hours to obtain "gyuhi" (a rice paste).

When the product prepared with anhydrous- or hydrous-crystalline trehalose was allowed to stand at 25° C. without packaging, a colony of a black mold was observed in the product with hydrous crystalline trehalose after 15 days of its processing, while no bacterial contamination was observed in the product with anhydrous crystalline trehalose even after 30 days of its processing.

The product with anhydrous crystalline trehalose after 30 days of its processing was cut into sections, and the sections were observed to find that the texture near the surface of the product exhibited only a slight solidification and had a crystalline trehalose, while the inner texture exhibited the same level of satisfiable semi-transparency, gloss and viscosity as the product immediately after its processing. An x-ray diffraction figure revealed that the crystalline trehalose was hydrous crystalline trehalose which had been converted from anhydrous crystalline trehalose.

As a result, it was revealed that anhydrous trehalose acts as a desiccant for gelatinized starch and prevents bacterial contamination, as well as the retrogradation of gelatinized starch. Anhydrous trehalose having these satisfiable properties can be favorably used in a variety of products prepared with gelatinized starch such as "gyuhi" and flour paste.

The preparation of powdery anhydrous trehalose according to the invention are described in the following Examples for reference:

Example for Reference 1

Hydrous crystalline trehalose was dissolved by heating in a small amount of water, and the resultant aqueous solution was placed in a vessel and boiled down in vacuo to obtain a syrup with a moisture content of 5.0%. The syrup was transferred to a crystallizer, mixed with one by weight of anhydrous crystalline trehalose as a seed crystal against the syrup, d.s.b., and allowed to crystallize trehalose at 120° C. for 5 minutes under stirring conditions. The resultant massecuite was transferred to an aluminum container and aged at 100° C. for 6 hours to form a block.

Figure 2:
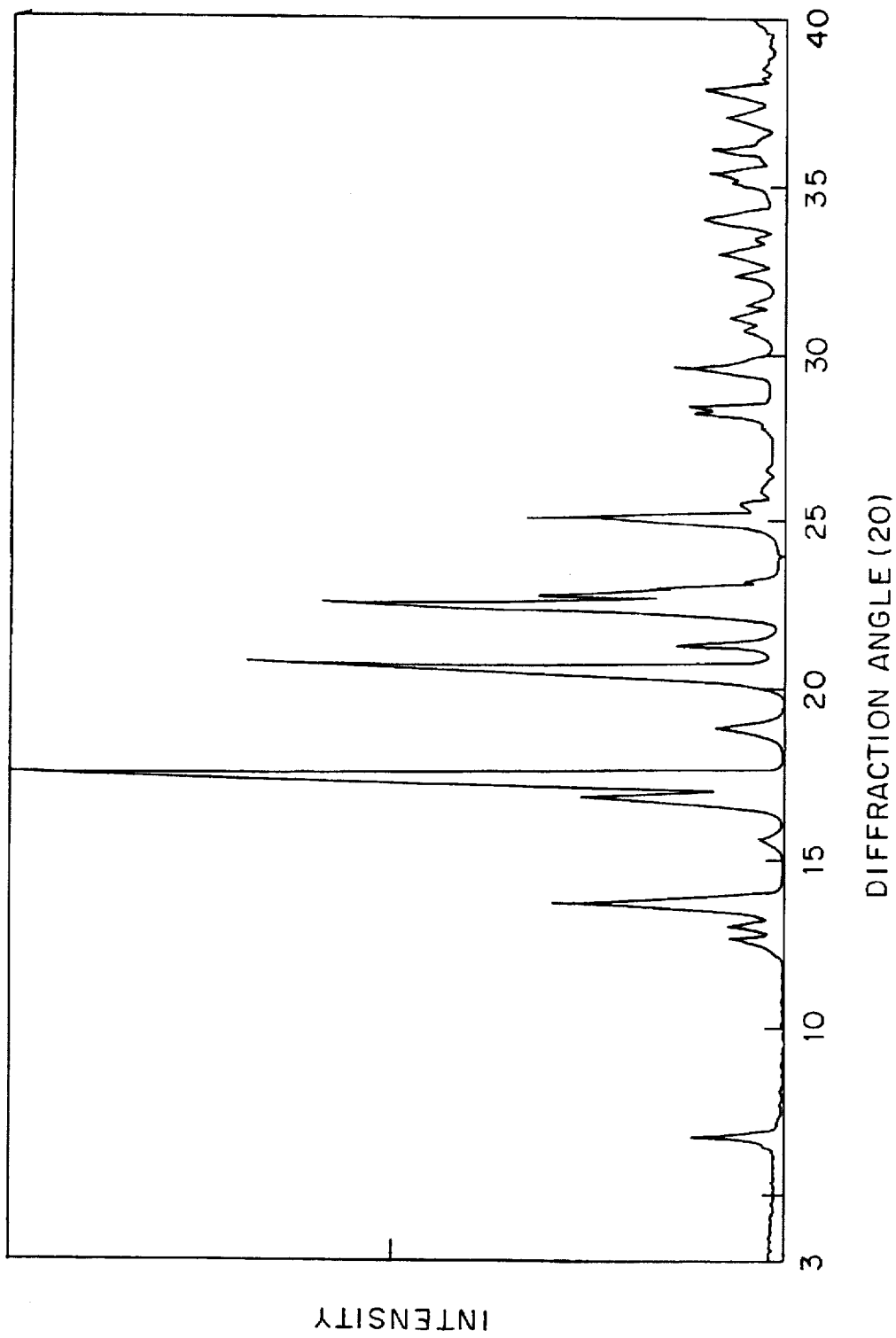
FIG. 2 shows a powder x-ray diffraction figure of anhydrous crystalline trehalose.

The resultant block was pulverized by a cutter into a powdery product which was then subjected to a fluidized-bed drying to obtain an anhydrous crystalline trehalose with a moisture content of 0.32% in the yield of about 87% against the material hydrous crystalline trehalose, d.s.b. The powder x-ray diffraction figure of the anhydrous crystalline trehalose was as shown in FIG. 2.

The product can be favorably used as a desiccant for hydrous matters such as food products, pharmaceuticals, cosmetics and their materials or intermediates, as well as a white powdery sweetener with a mild sweetness.

Example for Reference 2

An aqueous solution of a high-purity trehalose was placed in a vessel and boiled down in vacuo to obtain a syrup with a moisture content of 4.0%, which was then mixed with 5% by weight of anhydrous crystalline trehalose as a seed crystal against the syrup, d.s.b., and allowed to crystallize trehalose at 95° C. under stirring conditions. The resultant crystal was granulated by a granulator, aged, dried and pulverized by a pulverizer to obtain a powdery anhydrous crystalline trehalose with a moisture content of 0.53% in the yield of about 95% against the material trehalose, d.s.b.

Similarly as the powdery anhydrous crystalline trehalose obtained by the method in Example for reference 1, the product can be favorably used as a desiccant, as well as a sweetener for a variety of hydrous matters.

Example for Reference 3

Figure 3:
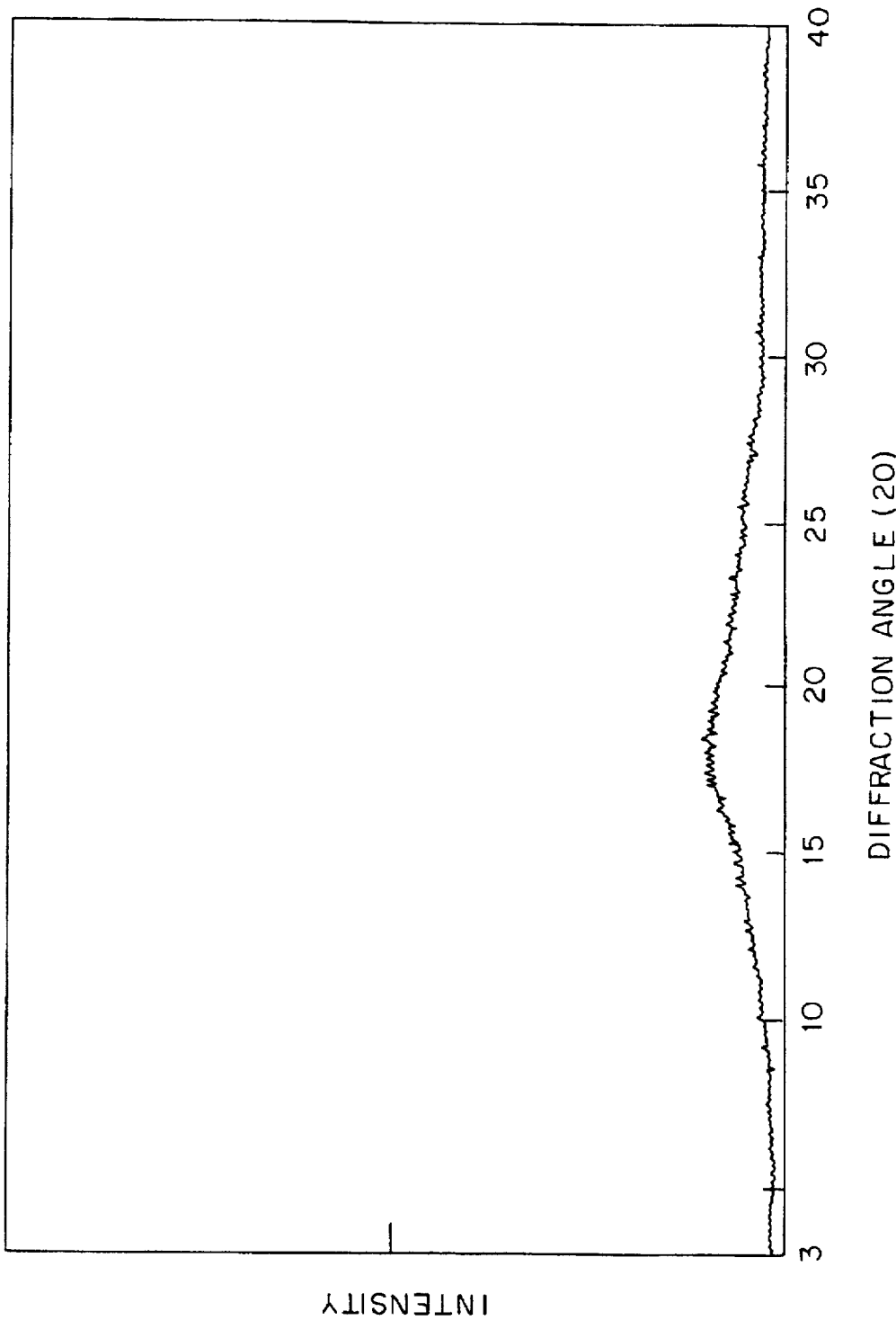
FIG. 3 shows a powder x-ray diffraction figure of anhydrous amorphous trehalose.

Hydrous crystalline trehalose was completely dissolved in water at an ambient temperature, and the resultant aqueous solution was dried in vacuo at 60° C. for 24 hours. The resultant dehydrated product was pulverized by a pulverizer to obtain an anhydrous amorphous trehalose with a moisture content of 0.83% in the yield of about 89% against the material hydrous crystalline trehalose, d.s.b. The powder x-ray diffraction figure of the anhydrous amorphous trehalose was as shown in FIG. 3.

Similarly as the powdery anhydrous crystalline trehalose obtained by the method in Example for reference 1, the product can be favorably used as a sweetener, as well as a desiccant for a variety of hydrous matters.

The examples and advantageous effects of the present invention are disclosed hereinafter:

Example 1

Desiccant

Twenty 9 aliquots of an anhydrous crystalline trehalose, obtained by the method in Example for reference 1, were injected into moisture-permeable small paper-bags to obtain a desiccant. The product can be favorably used as a desiccant to dehydrate the atmosphere in a moistureproof package injected with a dehydrated food product such as a cookie or a toasted and seasoned laver. Dehydrated- and oily-food products can be stably stored by using the product in combination with an oxygen scavenger.

Example 2

"Soboro-gyuhi" (A Starch Paste)

Four parts by weight of a powdery glutinous rice was suspended in 6 parts by weight of water, and the resultant suspension was poured onto a wet cloth covered over the inside surface of a wooden container, steamed at 100° C. for 20 minutes, mixed with one part by weight of sucrose and 7 parts by weight of an anhydrous crystalline trehalose obtained by the method in Example for reference 1, and further sufficiently mixed with 2 parts by weight of a starch hydrolyzate. The resultant mixture was formed and allowed to stand at an ambient temperature for 16 hours to convert the anhydrous trehalose into hydrous crystalline trehalose on the surface of the resultant product, which was then mildly rolled to form cracks on its surface to obtain the captioned product. The product had a satisfiable flavor and retained its high quality for a relatively-long period of time without substantial bacterial contamination.

Example 3

Confectionery Made of Sweet Potato

A sweet potato was sliced into thin pieces about 1-cm thick, and the pieces were steamed, cooled at ambient temperature, and dehydrated by dusting over them with an anhydrous crystalline trehalose prepared by the method in Example for reference 1 to convert the anhydrous crystalline trehalose into hydrous crystalline trehalose. Thus, the captioned product, having hydrous crystalline trehalose adhered on its surface, was prepared. The product had a satisfactory flavor and stability.

Example 4

Brandy Powder

Ten parts by weight of pullulan was dissolved in 2 parts by weight of a brandy, and the resultant solution was mixed with 8 parts by weight of an anhydrous crystalline trehalose obtained by the method in Example for reference 2. The resultant mixture was transferred to a container, and allowed to stand for 2 days to form a block while allowing the anhydrous crystalline trehalose to convert into hydrous crystalline trehalose. The block was pulverized by a pulverizer and classified to obtain a brandy powder with a satisfactory flavor. The product is a flavored powder having an adequate sweetness and a sufficient brandy-flavor, and you can enjoy it in your mouth. The product can be favorably used as a flavor-imparting agent for tea, as well as a material for confectioneries such as a premix powder and candy. The product can be favorably formed into a granule or a tablet by a granulator or a tabletting machine.

Example 5

"Miso" Powder

Two parts by weight of "akamiso" (a kind of miso) was mixed with 5 parts by weight of an anhydrous crystalline trehalose prepared by the method in Example for reference 2, and the resultant mixture was poured onto a metal plate provided with semispheric depressions, allowed to stand at an ambient temperature overnight to solidify the mixture in the depressions. The solidified products in the depressions were removed therefrom to obtain solid products, about 4 g each, which were then subjected to a pulverizer to obtain the captioned product. The product can be favorably used as a seasoning in an instant noodle and instant soup. When the product is formed into a solid product, it can be used as a solid seasoning or a miso confectionery.

Example 6

Soy Sauce Powder

A mixture, consisting of 0.02 parts by weight of a commercially available hydrous crystalline trehalose and 4 parts by weight of an anhydrous crystalline trehalose prepared by the method in Example for reference 3, was sprayed with "usukuchi-shoyu" (a less-colored soy sauce) to give the final content of one part by weight while the mixture was moving on a conveyer belt, transferred to an ageing tower, and allowed to stand at 30° C. overnight to covert the anhydrous trehalose into hydrous crystalline trehalose. Thus, the captioned product was obtained. The product can be favorably used as a seasoning for an instant noodle or an instant soup.

Example 7

Egg-yolk Powder

An egg yolk prepared from a fresh egg was sterilized at 60°–64° C. by a plate-type heat sterilizer to obtain a liquid egg yolk. To one part by weight of the liquid egg yolk was added 4 parts by weight of an anhydrous crystalline trehalose prepared by the method in Example for reference 1, and, similarly as in Example 4 the resultant mixture was formed into a block which was then pulverized into an egg-yolk powder. The product can be favorably used as a material for confectioneries such as premix powders, ice products and emulsifiers, as well as baby foods and therapeutic nutrients such as intubation foods and orally administrable fluid-foods. The product can be favorably used as a skin refiner and a hair restorer.

Example 8

Yogurt Powder

Two parts by weight of plain yogurt was mixed with 8 parts by weight of an anhydrous crystalline trehalose prepared by the method in Example for reference 1, and, similarly as in Example 4 the resultant mixture was formed into a block which was then pulverized into a yogurt powder. The product had a satisfactory flavor and stably retained lactic acid bacteria alive for a relatively-long period of time. The product can be favorably used as a material for confectioneries such as premix powders, ice products, emulsifiers and baby foods, as well as therapeutic nutrients such as intubation foods and orally-administrable fluid-foods. The product can be favorably incorporated into margarine, whipped cream, spread, cheese cake and jelly to obtain a product having a yogurt-like flavor. The product can be formed by a granulator or a tabletting machine into a preparation of lactic acid bacteria which can be favorably used as an agent for intestinal disorder.

Example 9

Hot Cake Mix

A hot cake mix was obtained by mixing 200 parts by weight of a wheat flour with 60 parts by weight of an egg yolk powder prepared by the method in Example 7, 25 parts by weight of butter, 10 parts by weight of sugar, 12 parts by weight of a baking powder and 0.5 parts by weight of salt. The product can be readily cooked into a hot cake having a satisfactory flavor by mixing the product with water or milk and baking the resultant mixture.

Example 10

Ginseng Extract Powder

A half part by weight of ginseng extract was kneaded with 1.5 parts by weight of an anhydrous crystalline trehalose prepared by the method in Example for reference 2, and, similarly as in Example 4 the resultant mixture was formed into a block and pulverized to obtain the captioned product. The product was subjected to a granulator together with adequate amounts of powdery vitamins B1 and B2 to obtain a granular ginseng extract containing vitamins. The product can be favorably used as a fatigue-removing agent, restorative and tonic.

Example 11

Solid Preparation for Fluid Food

A composition consisting of 500 parts by weight of an anhydrous crystalline trehalose prepared by the method in Example for reference 2, 270 parts by weight of an egg yolk powder prepared by the method in Example 7, 209 parts by weight of a defatted milk, 4.4 parts by weight of sodium chloride, 1.85 parts by weight of potassium chloride, 0.01 part by weight of thiamine, 0.1 part by weight of sodium L-ascorbate, 0.6 parts by weight of vitamin-E acetate and 0.04 parts by weight of nicotinic acid amide was prepared, and 25 g aliquots of the composition were injected into small moistureproof aluminum bags, and heat sealed to obtain the captioned product.

The product, wherein the moisture content in the atmosphere of the bag is decreased, does not require cold storage and has a satisfactory stability for a relatively-long period of time even at an ambient temperature. The solubility and dispersibility in water are satisfactory. In use, one bag of the product is dissolved in about 150–300 ml water into a fluid food prior to oral administration to the body or intubation into the nasal cavity, stomach and intestine.

Example 12

Solid Pharmaceutical Preparation

New born hamsters were injected with an antiserum prepared from rabbits by conventional method in order to reduce their immunoreaction, subcutaneously transplanted with BALL-1 cells, and fed for 3 weeks in usual manner. Subcutaneously-formed tumors in the hamsters were extracted and cut into pieces which were then dispersed and suspended in physiological saline. The resultant cells were washed with RPMI 1640 medium (pH 7.2) free of serum, resuspened in a fresh preparation of the same medium to give a concentration of about $2 \times 10^6$ cells/ml, and kept at 35° C.

To the cell suspension was added 200 IU/ml human interferon-α, incubated for about 2 hours, mixed with about 300HA (hemagglutination titer)/ml of Sendal virus (HVJ), and further incubated for 20 hours to induce human interferon-α. The resultant culture was centrifuged at about 1,000 ×g and about 4° C. to remove sediment. The supernatant thus obtained was membrane filtered, and the resultant filtrate was fed to a column of an immobilized anti-interferon-α antibody. The column was fed with a buffer to remove a non-adsorbed fraction, followed by eluting an adsorbed fraction from the column and concentrating the fraction into a solution of about 0.01 w/v % human interferon-α having a specific activity of about $2 \times 10^8$ IU/mg protein in the yield of about 4 ml per hamster.

Six g aliquots of a pyropen-free anhydrous crystalline trehalose, prepared by the method in Example for reference 1, were placed in 100-ml moistureproof plastic bottles, and injected with 0.2 ml aliquots of the solution containing about $4 \times 10^6$ IU of human interferon-α, followed by aseptically capping the bottles with rubber stoppers and cap-sealing them. Thus, the captioned product was obtained. According to the preparation, a solution containing human interferon-α is simply dehydrated only by contacting it with a powdery anhydrous trehalose so that none of treatment, apparatus and energy requisite for general lyophilization are required, and the human interferon-α is effectively stabilized.

The product readily dissolves in water, and this renders it advantageously useful in an injection for an instillation or an intramuscular injection as an agent for anti-susceptive diseases which can be prevented and/or treated with human interferon-α, for example, an anti-virus agent, anti-tumor agent and agent of anti-rheumatism. The product can be suitably used as an internal medicine, as well as an agent for oral cavity. The product can be also used as a diagnostic reagent.

Example 13

Solid Pharmaceutical Preparation

A seed culture of BALL-1 cell derived from human lymphoblastoid was inoculated into Eagle's minimum essential medium (pH 7.4) supplemented with 20% fetal calf serum, and subjected to a suspension culture in vitro at 37° C. in the usual manner. The resultant cells were washed with serum-free Eagle's minimum essential medium (pH 7.4), and resuspended in a fresh preparation of the same medium to give a concentration of about $1 \times 10^7$ cells/ml. To the cell suspension was added about 1,000HA/ml of HVJ, and incubated at 38° C. for one day to induce human tumor necrosis factor-α (hTNF-α). The resultant culture was centrifuged at about 1,000 ×g and 4° C. to obtain a supernatant which was then dialyzed against a physiological saline (pH 7.2) containing 0.01M phosphate buffer for 15 hours, and membrane filtered. The filtrate thus obtained was fed to a column of an anti-interferon antibody, and a non-adsorbed fraction was recovered and purified on an affinity chromatography using a column of an anti-tumor necrosis factor-α monoclonal antibody, followed by concentrating the resultant into a 0.01 w/v % solution of hTNF-α having a specific activity of about $2 \times 10^6$ JRU (Japan reference unit)/mg protein. The yield of hTNF-α was about $5 \times 10^4$ JRU per one L of the cell culture.

Ten g aliquots of an anhydrous crystalline trehalose, prepared by the method in Example for reference 1, were injected into 100-ml vials which were then injected with 0.5 ml aliquots of the solution containing about $1 \times 10^5$ JRU of hTNF-α, aseptically capped with rubber stoppers, and cap sealed to obtain the captioned product. Since a solution containing hTNF-α is dehydrated by a powdery anhydrous trehalose in the above-mentioned preparation, no treatment such as a lyophilization is required and hTNF-α is effectively stabilized.

The product readily dissolves in water, and this renders it advantageously useful in an injection for instillation or an intramuscular injection as an agent for anti-susceptive diseases which can be prevented and/or treated with hTNF-α, for example, an anti-virus agent, anti-tumor agent, agent of anti-ascites and agent of anti-immunopathy. The product can be suitably used as an internal medicine, as well as an agent for oral cavity. The product can be also used as a diagnostic reagent.

Example 14

Ointment for Treating Skin Trauma

Three parts by weight of iodine was dissolved in 450 parts by weight of an anhydrous crystalline trehalose prepared by the method in Example for reference 2, and the solution was admixed with 50 parts by weight of methanol. The resultant solution was admixed with 200 parts by weight of 10% aqueous pullulan solution and 50 parts by weight of hydrous maltose, and the resultant mixture was allowed to stand at an ambient temperature overnight to convert the anhydrous trehalose into hydrous crystalline trehalose. Thus, an ointment for treating skin trauma having a satisfactory extensibility and adhesion was obtained.

The product heals trauma such as an ulcer caused by a cut, abrasion, burn and dermatophytosis. The product exerts the inherent bactericidal activity of iodine, and acts as a nutrient-supplementing agent for living cells because it contains trehalose. Thus, the product shortens a period required for such a treatment and heals a wounded part thoroughly.

As described above, the present invention relates to a desiccant comprising a non-reducing anhydrous trehalose as an effective ingredient. The desiccant can be suitably used to decrease the moisture content in atmosphere of a moisture-proof package injected with a dehydrated food product, as well as to decrease the moisture content in a hydrous matter such as food products, pharmaceuticals, cosmetics, products of chemical engineering, and their materials or intermediates. The method according to the present invention, which contains a step of dehydrating a hydrous matter by incorporating anhydrous trehalose into the hydrous matter to convert the anhydrous trehalose into hydrous crystalline trehalose, attains a substantial decrease of the moisture content in the hydrous matter, and does not require severe conditions such as heat drying. Thus, high-quality dehydrated products are readily prepared by the present invention without deteriorating the quality of hydrous matters such as food products which readily lose their flavors and tastes, as well as pharmaceuticals which are susceptible to decomposition and reduction of their effective components. The dehydrated products thus obtained have a relatively-high stability and a relatively-long shelf-life because they are prevented from bacterial contamination, as well as deterioration and alteration such as hydrolysis, acidification and browning.

While a preferred embodiment of the invention has been illustrative purpose only, and it is to be understood that changes and variations may be made without departing from the spirit or scope of the following claims.

We claim:

1. A dehydrated product containing hydrous trehalose with or without anhydrous trehalose which product is obtained by adding 0.01 to 200 parts by weight of anhydrous trehalose to one part by weight of a hydrous matter to dehydrate the hydrous matter while converting the anhydrous trehalose to hydrous trehalose, wherein said anhydrous trehalose is selected from the group consisting of anhydrous crystalline trehalose, anhydrous amorphous trehalose and mixtures thereof;

and wherein said anhydrous crystalline trehalose is obtained by:

providing a syrupy aqueous solution of trehalose with a moisture content lower than 10 w/w%;

maintaining said syrupy aqueous solution of trehalose at a temperature in the range of 50°–160° C. in the presence of a seed crystal in order to crystallize anhydrous crystalline trehalose; and recovering the resultant anhydrous crystalline trehalose; and wherein said anhydrous amorphous trehalose is obtained by drying a syrupy aqueous solution of trehalose or a hydrous crystalline trehalose, and recovering the resultant anhydrous amorphous trehalose.

2. The product of claim 1 wherein said hydrous matter contains at least one member selected from the group consisting of gelatinized starch, alcohols, oil-soluble substances and biologically active substances.

3. The product of claim 1 wherein said hydrous matter is a food.

4. The product of claim 1 wherein said hydrous matter is a pharmaceutical.

5. The product of claim 1 wherein said hydrous matter is a cosmetic.

6. The product of claim 1 wherein said anhydrous trehalose entraps about 10 w/w% moisture from said hydrous matter.

7. A method for preventing the retrogradation of an amylaceous substance, which comprises a step of incorporating an effective amount of anhydrous trehalose into an amylaceous substance.

8. The method of claim 7, wherein 0.01–200 parts by weight of said anhydrous trehalose is incorporated into one part by weight of an amylaceous substance.

9. The method of claim 7, wherein said anhydrous trehalose is selected from the group consisting of anhydrous crystalline trehalose, anhydrous amorphous trehalose, and mixtures thereof.

10. The method of claim 9, wherein said anhydrous crystalline trehalose is obtained by:

providing a trehalose syrup with a moisture content lower than 10 w/w %;

maintaining said syrup at a temperature in the range of 50°–160° C. in the presence of a seed crystal in order to crystallize anhydrous crystalline trehalose; and recovering the resultant anhydrous crystalline trehalose.

11. The method of claim 7, wherein said anhydrous amorphous trehalose is obtained by drying a trehalose syrup or a hydrous crystalline trehalose, and recovering the resultant anhydrous amorphous trehalose.

12. The method of claim 7, wherein said amylaceous substance is gelatinized starch.

* * * * *